(12) United States Patent
Tian et al.

(10) Patent No.: US 10,011,818 B2
(45) Date of Patent: Jul. 3, 2018

(54) METHOD FOR IN VITRO OOCYTE MATURATION

(71) Applicant: CHINA AGRICULTURE UNIVERSITY, Beijing (CN)

(72) Inventors: Jianhui Tian, Beijing (CN); Zhenwei Jia, Beijing (CN); Jiaxin Zhang, Beijing (CN); Lei An, Beijing (CN); Zhonghong Wu, Beijing (CN)

(73) Assignee: China Agriculture University, Beijing (CN)

( * ) Notice: Subject to any disclaimer, the term of this patent is extended or adjusted under 35 U.S.C. 154(b) by 0 days.

(21) Appl. No.: 14/860,814

(22) Filed: Sep. 22, 2015

(65) Prior Publication Data

US 2016/0032243 A1 Feb. 4, 2016

Related U.S. Application Data

(63) Continuation-in-part of application No. 14/429,065, filed as application No. PCT/CN2012/001633 on Dec. 6, 2012.

(30) Foreign Application Priority Data

Sep. 18, 2012 (CN) .......................... 2012 1 0348285

(51) Int. Cl.
*C12N 5/075* (2010.01)
(52) U.S. Cl.
CPC ........ *C12N 5/0609* (2013.01); *C12N 2501/11* (2013.01); *C12N 2501/31* (2013.01); *C12N 2501/998* (2013.01); *C12N 2517/10* (2013.01)
(58) Field of Classification Search
None
See application file for complete search history.

(56) References Cited

FOREIGN PATENT DOCUMENTS

WO WO 0176360 A2 * 10/2001 ........... C12N 5/0609

OTHER PUBLICATIONS

Kawamura, K. et al. Aug. 23, 2011. Pre-ovulatory LH/hCG surge decreases C-type natriuretic peptide secretion by ovarian granulosa cells to promote meiotic resumption of pre-ovulatory oocytes. Human Reproduction 26(11): 3094-3101. specif. pp. 3094, 3095, 3096.*
Younis, A.I. et al. 1989. Influence of serum and hormones on bovine oocyte maturation and fertilization in vitro. Gamete Research 23: 189-201. specif. pp. 189, 190, 193.*
Sato, Y. et al. May 2012. C-type natriuretic peptide stimulates ovarian follicle development. Molecular Endocrinology 26: 1158-1166. specif. pp. 1158, 1160, 1161, 1163.*
Bilodeau-Goeseels, Cows are not Mice: The Role of Cyclic AMP, Phosphodiesterases, and Adenosine Monophosphate-Activated Protein Kinase in the Maintenance of Meiotic Arrest in Bovine Oocytes, Molecular Reproduction & Development 78:734-743 (2011).
Franciosi et al., "Natriuretic Peptide Precursor C Delays Meiotic Resumption and Sustains Gap Junction-Mediated Communication in Bovine Cumulus-Enclosed Oocytes", Biology of Reproduction (2014) 91(3):61, 1-9.
Tornell, et al., "Atrial Natriuretic Peptide Inhibits Spontaneous Rat Oocyte Maturation", Endocrinology, (1990);126(3):1504-8.
Zhang, et al., "Atrial Natriuretic Peptide Inhibits the Actions of FSH and Forskolin in Meiotic Maturation of Pig Oocytes via Different Signalling Pathways", Journal of Molecular Endocrinology (2005) 34, 459-472.
Zhang, et al., "Granulosa Cell Ligand NPPC and Its Receptor NPR2 Maintain Meiotic Arrest in Mouse Oocytes", Science 330, (2010), 366-369.
Fair T, Hyttel P, Motlik J, Boland M, Lonergan P., Maintenance of meiotic arrest in bovine oocytes in vitro using butyrolactone I: effects on oocyte ultrastructure and nucleolus function. Mol Reprod Dev 2002; 62 (3):375-386.
Lonergan P, Faerge I, Hyttel PM, Boland M, Fair T., Ultrastructural modifications in bovine oocytes maintained in meiotic arrest in vitro using roscovitine or butyrolactone. Mol Reprod Dev 2003; 64 (3):369-378.
Alexander B, Coppola G, Di Berardino D et al., The effect of 6-dimethylaminopurine (6-DMAP) and cycloheximide (CHX) on the development and chromosomal complement of sheep parthenogenetic and nuclear, 2006.
Vaknin KM, Lazar S, Popliker M, Tsafriri A. Role of meiosis-activating sterols in rat oocyte maturation: Effects of specific inhibitors and changes in the expression of lanosterol 14 alpha-demethylase during the preovulatory period. Biol Reprod 2001; 64 (1):299-309.
Robinson JW, Zhang M, Shuhaibar LC et al., Luteinizing hormone reduces the activity of the NPR2 guanylyl cyclase in mouse ovarian follicles, contributing to the cyclic GMP decrease that promotes resumption of meiosis in oocytes. Dev Biol 2012; 366 (2):308-316.
Lee KB, Zhang M, Sugiura K et al., Hormonal coordination of natriuretic peptide type C and natriuretic peptide receptor 3 expression in mouse granulosa cells. Biol Reprod 2013; 88 (2):42.
Zhang M, Su YQ, Sugiura K et al., Estradiol promotes and maintains cumulus cell expression of natriuretic peptide receptor 2 (NPR2) and meiotic arrest in mouse oocytes in vitro. Endocrinology 2011; 152 (11):4377-4385.

* cited by examiner

*Primary Examiner* — Renee Claytor
*Assistant Examiner* — Sharon M. Papciak
(74) *Attorney, Agent, or Firm* — Pearl Cohen Zedek Latzer Baratz LLP

(57) ABSTRACT

Methods are provided for in vitro maturation (IVM) of bovine oocytes that include steps of (a) pre-culturing bovine germinal vesicle (GV) oocytes in the presence of C-type natriuretic peptide (CNP) and (b) subsequently culturing the oocytes of (a) for an extended duration in medium containing follicle stimulating hormone (FSH), luteinizing hormone (LH), 17β-estradiol (E2), epidermal growth factor (EGF), and fetal bovine serum (FBS).

3 Claims, No Drawings

METHOD FOR IN VITRO OOCYTE MATURATION

CROSS-REFERENCE TO RELATED APPLICATIONS

This application is a Continuation in Part of U.S. patent application Ser. No. 14/429,065, filed Jul. 16, 2015, which is a National Phase Application of PCT International Application No. PCT/CN2012/001633, International Filing Date Dec. 6, 2012, which are hereby incorporated by reference.

FIELD OF THE INVENTION

The invention relates to a novel method for in vitro maturation (IVM) of bovine oocytes. Specifically, the invention relates to the application of C-type natriuretic peptide (CNP) in method for IVM of bovine oocytes. The invention provides a method for producing high-quality IVM oocytes, which can be used in livestock propagation through in vitro fertilization (IVF), as well as production of cloned or transgenic animals. The invention herein belongs to the field of embryo biotechnology.

BACKGROUND OF THE INVENTION

In vitro embryo production (IVP), which comprises in vitro oocyte maturation (IVM), in vitro fertilization (IVF) and in vitro embryo culture (IVC), holds many benefits in agricultural livestock settings, facilitating the mass production of embryos at low cost. From 2010 to 2012, the amount of transferred IVP bovine embryos has been raised over eight times, reaching 350,000 annually. Moreover, commercial bovine IVP embryo transfer has become a large international business to reduce costs of genetic export and import (2013). However, the existing methods for IVM of bovine oocytes, always lead to nuclear-cytoplasmic asynchrony, which would compromise cytoplasmic maturation of oocytes and subsequent embryonic development. Therefore, nuclear-cytoplasmic asynchrony of IVM oocyte is the primary bottleneck for the large-scale application of IVP process in enhancing bovine reproductive efficiency.

Efficient IVP process is largely dependent on the fully matured oocytes. The oocytes used for IVM were mainly collected from ovaries by ovum pick-up (OPU) or from slaughtered animals. Distinct with naturally (in vivo) matured oocytes, the oocytes used for IVM are recovered from 3-8 mm follicles. In these follicles, immature oocytes are maintained at meiotic arrest, which is also referred as germinal vesicle (GV) stage. The isolation of GV oocyte from its follicular environment triggers meiotic resumption (also referred to as "spontaneous nuclear maturation"). During the process of conventional IVM, spontaneous nuclear maturation causes a premature breakdown of oocyte-cumulus cell gap junctions (Thomas et al., 2004), which impairs the intercellular transport of beneficial cumulus cell metabolites to oocytes (Gilchrist and Thompson, 2007). Therefore, the conventional IVM systems always lead to an insufficient cytoplasmic maturation in large part of oocytes that nuclear maturation are fully achieved. This is referred as "nuclear-cytoplasmic asynchrony".

Numerous efforts have been made to overcome the nuclear-cytoplasmic asynchrony of IVM oocytes. Many chemical agents that could inhibit oocyte meiotic resumption, were used to inhibit spontaneous maturation temporarily and thus improve the synchronization between nuclear and cytoplasmic maturation, which could enhance developmental competence of oocytes. These chemicals, such as roscovitine, butyrolactone (Mermillod et al., 2000), cycloheximide (Kastrop et al., 1991), 6-DMAP (Saeki et al., 1997), forskolin (Albuz et al., 2010), etc., always showed evident inhibitory effect on nuclear maturation. Furthermore, some of those meiotic inhibitors could improve subsequent developmental rate of preimplantation embryos. However, the safety of these agents for oocytes and embryos has not been fully evaluated and certain of agents have been identified to have detrimental effects on oocyte ultrastructure and function (Fair et al., 2002; Lonergan et al., 2003). Furthermore, inappropriate usage of chemical agents during oocyte IVM could subsequently impair implantation and fetal development after embryo transfer (Albuz et al., 2010).

Therefore, safe, efficient and reversible oocyte meiotic inhibition during IVM is critical for oocyte cytoplasmic maturation and subsequent embryonic development. It would be desirable if endogenous physiological factors responsible for oocyte meiotic arrest could be used for inhibiting spontaneous meiotic resumption, thereby improving nuclear-cytoplasmic synchronization and subsequent developmental competence of IVM oocytes.

C-type natriuretic peptide (CNP), encoded by the natriuretic peptide precursor C (Nppc) gene, is an essential factor for maintaining oocyte meiotic arrest. In bovines, we have demonstrated an efficient and essential role of CNP in maintaining oocyte meiotic arrest. CNP derived from MGCs targets directly the NPR2 localized on both cumulus cells (CCs) and oocytes, and thus increase intra-oocyte cGMP levels via both CC-dependent and independent pathways. After that, increased intra-oocyte cGMP levels leads to an elevation of intra-oocyte cAMP levels by inhibiting PDE3A, and thus maintains oocyte meiotic arrest. This mechanism is very distinct from that reported in mice and porcines, in which only CC-dependent pathway functions via gap junctions (Zhang et al., 2010; Hiradate et al., 2014).

Based on the direct and efficient inhibitory effect on meiotic resumption in bovine oocytes, CNP could be a potential candidate for improving IVM method. Until the application of the invention, CNP, as a naturally presented factor in follicle fluid, has not been used for improving oocyte IVM methods.

SUMMARY OF THE INVENTION

It is therefore an object of the present invention to develop a novel method for IVM of bovine oocytes.

It is another object of the present invention to apply CNP in improving IVM culture medium of bovine oocytes.

It is further an object of the present invention to develop an IVM culture medium which could enhance developmental competence of IVM bovine oocytes and subsequent embryonic development.

The present invention is directed to a novel biphasic IVM system, which comprises a CNP-based pretreatment (pre-IVM) phase, followed by an extended-IVM phase. The development of this novel system is based on our study of mechanism for CNP-induced meiotic arrest in bovine oocytes, which is very distinct to that in mice and porcine.

The use of CNP in IVM culture medium is superior to other chemical meiosis inhibitor, such as roscovitine, butyrolactone, cycloheximide, 6-DMAP, etc. As a molecule that is naturally present in the follicular fluid, CNP doesn't show any evident adverse effect on bovine oocytes and subsequent preimplantation embryos. Further more, by monitoring fetal development after embryo transfer and offspring growth, we could also excluded the possible long-term detrimental effects of CNP. Meanwhile, its efficient and reversible inhibitory effect on spontaneous meiotic resumption provides a alternative for improving existing IVM system of bovine oocytes.

The present invention specifically provides a novel IVM method for bovine oocytes, which comprises two phases: the first phase directs a pre-IVM culture medium containing CNP. Furthermore, our study indicates that the inhibitory effect of CNP on bovine oocyte meiotic resumption is dose-dependent. Preferably, oocytes resumption during IVM could significantly inhibited by pretreatment with CNP (pre-IVM) at the concentration in the range of 100-400 nM, more especially at 200 nM. While with higher concentration than 400 nM or lower than 100 nM, no evident inhibitory effect could be observed. It should also be noted that the preferable concentration of CNP in maintaining oocyte meiotic arrest is variable between different species. In mice, the preferable concentration of CNP for meiotic inhibition is 100 nM, and the inhibitory effect shows a increased trend with the elevated concentrations (Zhang et al., 2010).

Moreover, the invention comprises a pre-IVM culture medium for bovine oocytes. Preferably, the pre-IVM culture medium used herein is TCM-199 (tissue culture medium-199) that contains CNP at concentration of 100-400 nM, and BSA at concentration of 2.5-3.5 mg/ml. More especially, CNP at concentration of 200 nM, and BSA at concentration of 3 mg/ml would be more preferable.

The novel IVM method for bovine oocyte provided in the invention comprises two phases (biphasic IVM system): CNP-based pretreatment phase, followed by the extended IVM phase. Preferably, the extended IVM culture medium used herein is TCM-199 that contains 8-12 µg/ml FSH, 0.8-1.2 µg/ml LH, 0.8-1.2 µg/ml E2, 8-1.2 ng/ml EGF, 8-12% FBS.

Further, the preferable duration of pre-IVM is 5-7 hours, while the preferable duration of extended IVM phase is 24-28 hours. It must be noted that the extended IVM is required for enhancing developmental competence of matured oocytes. In Franciosi's study, CNP pretreatment (100 nM) alone could not lead to an evidently satisfying results of oocyte maturation and embryonic development (Franciosi et al., 2014).

Preferably, the oocytes used for IVM are collected from ovaries by OPU or from slaughtered animals.

Specially, the term "CNP" is also applicable for other type of peptides or derivates that have inhibitory effect on oocyte meiotic resumption.

DETAILED DESCRIPTION OF THE INVENTION

The following embodiment should be considered as a detailed description of the invention, but not the limiting description. Any changes or modifications based on the invention, belongs to the definition of the invention.

1. Detailed Methods (1) Collection of Oocytes

Bovine ovaries were obtained from a local slaughterhouse, transported at 30-35° C. to the laboratory within 1 hour, and washed in warmed normal saline containing 2% Penicillin G-Streptomycin. Ovarian antral follicles (3-8 mm) were aspirated using an 18-gauge needle. cumulus-oocyte complexes (COCs) with homogenous oocyte cytoplasm and complete, compacted, and multilayered CCs (Grade-1) or complete but fewer than three layers of CCs (Grade-2), were collected using micropipettes.

(2) Pretreatment (Pre-IVM) of Oocytes with CNP

Grade-1 and -2 COCs were washed in the washing buffer (HEPES-TCM199) for three times, and then washed in pre-IVM medium (TCM199 containing 3 mg/ml BSA and CNP at different concentrations (50, 100, 200 and 400 nM) for two times. After that, COCs were transfer into pre-IVM medium (pre-warmed for 2 hours) in 4-well plate (500 µl pre-IVM medium and 50 COCs in each well) and cultured for 6 hours at 38.5° C., in humidified air with 5% $CO_2$. After pre-IVM phase, a proportion of COCs are digested with hyaluronidase to remove cumulus cells. To determine the most preferable concentration of CNP for pre-VIM, meiosis kinetics of oocytes was evaluated according to nuclear morphology using DAPI staining under a fluorescence microscope. The oocytes without pre-IVM phase are used as control.

(3) Extended-IVM of Oocytes.

After cultured in pre-IVM medium containing 200 nM CNP, COCs are further cultured in extended-IVM medium (TCM199 supplemented with 10 µg/ml FSH, µg/ml LH1, 1 µg/ml E2, 10 ng/ml EGF, 10% FBS) at 38.5° C., in humidified air with 5% $CO_2$. To determine the most preferable duration for extended-IVM, COCs were cultured for 24, 26 or 28 hours. In addition, COCs without pre-IVM phase, are also cultured in pre-IVM medium for 24, 26 or 28 hours as controls.

(4) In Vitro Fertilization and Culture

After maturation, the COCs were fertilized in BO medium for 8 hours at 39° C. under 5% CO2 in a humidified atmosphere. After fertilization, the presumptive zygotes were transferred to 100 µl CR1 culture medium droplets (15 zygotes in each droplets) at 39° C. in a humidified atmosphere. The culture medium was changed every 2 days during the culture period. The percentage cleavage and rates of subsequent embryo development to the blastocyst stage were recorded on day 2 and 7, respectively.

2. Results (1) Effect of CNP at Different Concentrations on Spontaneous Meiotic Resumption of IVM Oocytes The inhibitory effect of CNP on meiotic resumption of bovine oocytes shows dose-depended patterns, with maximal effect at 200 nM. The rate of oocytes maintaining at GV stage is significant higher than that in control group (P<0.01) (Table 1). However, higher CNP concentrations do not show increased inhibitory effect.

TABLE 1

The effect of pretreatment with CNP at different concentrations on the meiotic resumption of bovine oocytes

| Treatments | No. of oocytes | No. of GV oocytes (%) | No. of GVBD oocytes (%) |
| --- | --- | --- | --- |
| Control | 91 | 51 (56 ± 2.6$^c$) | 40 (44 ± 2.6$^c$) |
| CNP (50 nM) | 101 | 64 (63.4 ± 3.1$^{bc}$) | 37 (21.3 ± 3.1$^{bc}$) |
| CNP (100 nM) | 98 | 68 (69.4 ± 2.6$^{abc}$) | 30 (30.6 ± 2.6$^{bc}$) |
| CNP (200 nM) | 97 | 79 (81.4 ± 2.1$^a$) | 18 (19.6 ± 2.1$^a$) |
| CNP (400 nM) | 106 | 79 (74.5 ± 2.8$^{ab}$) | 27 (25.5 ± 2.8$^{ab}$) |

Table shows the mean ± SEM values of at least three independent experiments.
Data with different letters within same column are significantly different (p < 0.01)

(2) Effect of CNP Pre-IVM and Extended-IVM on Developmental Competence of Bovine Oocytes CNP pre-IVM shows a beneficial effect on developmental competence of IVM oocytes. After IVF, the cleavage rates of oocytes pre-treated with CNP and followed by a extended IVM phase are significantly higher that of their counterparts. In addition, our novel method significantly enhances blastocyst rates.

TABLE 2

Effect of CNP pre-treatment and extended IVM on developmental rate of bovine oocytes after IVF

| CNP based Pre-IVM phase | Extended-IVM or standard-IVM phase | No. of oocytes | No. of cleavage (%) | No. of blastocysts (%) |
|---|---|---|---|---|
| 0 h | 24 h | 251 | 190 (75.7 ± 2.7$^b$) | 58 (23.1 ± 2.3$^b$) |
|  | 26 h | 216 | 168 (77.8 ± 3.0$^b$) | 52 (24.7 ± 1.9$^b$) |
|  | 28 h | 198 | 143 (72.2 ± 3.4$^b$) | 42 (21.2 ± 2.4$^b$) |
| 6 h | 24 h | 193 | 157 (81.3 ± 2.7$^{ab}$) | 53 (27.5 ± 1.3$^{bc}$) |
|  | 26 h | 217 | 89 (87.1 ± 0.75$^a$) | 62 (28.6 ± 0.7$^c$) |
|  | 28 h | 214 | 186 (88.3 ± 3.0$^a$) | 80 (37.4 ± 2.5$^a$) |

Table shows the mean ± SEM values of at least three independent experiments.
Data with different letters within same column are significantly different ($p < 0.01$)

What is claimed is:

1. A method for in vitro maturation (IVM) of bovine oocytes, comprising:
   (a) pre-culturing one or more bovine germinal vesicle (GV) oocytes in a pre-IVM culture medium that comprises a meiosis-inhibiting concentration of C-type natriuretic peptide (CNP), under conditions and for a time sufficient to obtain bovine oocytes in meiotic arrest; wherein the pre-IVM culture medium comprises 200 nM CNP and 3 mg/ml BSA; wherein the step of pre-culturing is for 6 hours at 38.5° C., in humidified air with 5% $CO_2$; and
   (b) subsequently culturing the bovine oocytes in meiotic arrest obtained in step (a) for 28 hours in an extended-IVM culture medium containing follicle stimulating hormone (FSH), luteinizing hormone (LH), 17β-estradiol (E2), epidermal growth factor (EGF), and fetal bovine serum (FBS) to obtain matured bovine oocytes having enhanced developmental competence relative to bovine GV oocytes that have not been pre-cultured with CNP present.

2. The method of claim 1, wherein the extended-IVM culture medium comprises 8-12 μg/ml FSH, 0.8-1.2 μg/ml LH, 0.8-1.2 μg/ml E2, 8-12 ng/ml EGF, and 8-12% FBS.

3. The method of claim 2, wherein the extended-IVM culture medium comprises TCM-199.

* * * * *